United States Patent [19]
Kurosawa et al.

[11] Patent Number: 6,019,881
[45] Date of Patent: Feb. 1, 2000

[54] $NO_X$ SENSOR

[75] Inventors: Hideyuki Kurosawa; Masaharu Hasei; Yukio Nakanouchi, all of Kumagaya, Japan

[73] Assignee: Kabushiki Kaisha Riken, Tokyo, Japan

[21] Appl. No.: 09/160,344

[22] Filed: Sep. 25, 1998

Related U.S. Application Data

[63] Continuation of application No. 08/737,009, filed as application No. PCT/JP96/00537, Mar. 6, 1996, abandoned.

[30] Foreign Application Priority Data

Mar. 10, 1995 [JP] Japan ......................... 7-78427

[51] Int. Cl.⁷ .................................................. G01N 27/407
[52] U.S. Cl. ........................... 204/424; 204/426; 205/781
[58] Field of Search ..................... 204/421–429

[56] References Cited

U.S. PATENT DOCUMENTS

| | | | |
|---|---|---|---|
| 4,502,939 | 3/1985 | Holfelder et al. | 204/425 |
| 4,587,105 | 5/1986 | Bonne et al. | 204/426 |
| 4,720,335 | 1/1988 | Fukushima et al. | 204/421 |
| 5,037,525 | 8/1991 | Badwal | 204/424 |
| 5,397,442 | 3/1995 | Wachsman | 204/428 |

FOREIGN PATENT DOCUMENTS

| | | |
|---|---|---|
| 59-91358 | 5/1984 | Japan . |
| 61-184450 | 8/1986 | Japan . |
| 61-264250 | 11/1986 | Japan . |
| 8-5606 | 1/1996 | Japan . |
| 8-62174 | 3/1996 | Japan . |

OTHER PUBLICATIONS

Lawrenz et al;"Investigations on the determination of NO with galvanic $ZrO_2$ solid electrolyte cells"; Fresenius J. Anal Chem.; vol. 349, pp. 679–683, 1994, month unavailable.

Yao et al; "Use of Sodium Nitrite Auxiliary Electrode for Solid Electrolyte Sensor to Detect Notrogen Oxides"; Chem. Letters; pp. 587–590, 1992, month unavailable.

Shimizu et al; "Solid Electrolyte $NO_2$ Sensors Fitted with Sodium Nitrate and/or Barium Nitrate Electrodes"; Denki Kagaku; vol. 59, No. 6, pp. 465–472, 1991, month unavailable.

Murphy et al, "Foundation of College Chemistry", 2d ed., (1975), p. 90.

*Primary Examiner*—T. Tung
*Attorney, Agent, or Firm*—Kubovcik & Kubovcik

[57] ABSTRACT

The present invention discloses a $NO_x$ sensor consisting at least of a pair of the first and the second electrodes formed in touch with an oxygen conductive solid electrolyte; wherein at least the first elelctrode is composed of oxides of an element selected from 7a Group or 8 Group, especially from Mn, Fe, Co, and Ni or a substance containing said oxides or of hybrid oxides (including the one of oxygen deficiency expressed by $ABO_3$, $AB_2O_4$, $A_2BO_4$ and $ACBO_4$ including 7a Group and 8 Group. A $NO_x$ sensor acording to the present invention has a good sensitivity without being affected by the concentration of $CO_2$ and detects $NO_x$ concentration in an exhaust gas at a temperature above 600° C.

2 Claims, 4 Drawing Sheets

$NO_x$ SENSOR

This application is a continuation of application Ser. No. 08/737,009, filed Oct. 31, 1996, now abandoned, which is the national stage application in the U.S. of PCT International Application No. PCT/JP96/00537, filed Mar. 6, 1996.

FIELD OF THE INVENTION

The present invention relates to a sensor to detect $NO_x$ concentration in an exhaust gas generated from combustion furnace, automobile engine, etc.

PRIOR ART

Continuous monitoring, feedback control of the combustion condition based on the monitoring result or the optimalization of the control of the desulfurization equipment have been examined to reduce $NO_x$ exhausted from combustion furnace, automobile engine, etc. Therefore, a small sized solid and simple solid type sensor with high sensitivity is needed to be used for the control. Especially, for the feedback of the combustion condition, a sensor which works stably in a high temperature exhausted gas of several hundreds ° C.

A semiconductor type sensor utilizing a phenomena that the electric resistance of a gas sensor composed of oxide semiconductor changes in proportion to the concentration of $NO_x$ or a solid electrolyte sensor measuring the electromotive force caused by the difference in the partial pressure of a gas at each electrodes which are formed on an ion conductive solid electrode are the representative sensors being proposed up to now.

However, there is a drawback in a semiconductor type sensor that enough sensitivity can not be obtained at a temperature above 500° C. where the physical absorption of the test gas does not occur, since it utilize the phenomena of the change of electric resistance of the gas sensor caused by the physical absorption.

On the other hand, a solid electrolyte sensor, using AgI or $RbAg_4 I_5$ as a solid electrolyte and an electrode coated by silver nitrate is disclosed (The Japanese Laid-open Patent Publication Sho61-184450). This sensor is a concentration cell type, wherein Ag ion in the nitrate migrates in the solid electrolyte by the difference of $NO_x$ concentration between the electrodes and causes the eletromotive force which complys with Nernst formula and detects $NO_x$ concentration by the measurement of said electromotive force. A concentration cell type sensor based on the same principle using NASICON ($Na_3 Zr_2 Si_2 PO_{12}$) as a solid electrolyte and $NaNO_3$ as electrodes is disclosed. (Chemistry Letters, vol.1, p.587 (~590 (1992)) Furthermore, a concentration cell using Na ion conductive β/β" alumina orβ/β" alumina, in which Na ion is replaced by Ba ion and using $Ba(NO_3)_2$ or mixture of $NaNO_3$ and $Ba(NO_3)_2$ as an electrode is disclosed in Denki Kagaku, vol.59, (1991) p.465~472.

In these sensors which detect $NO_x$ concentration by the measurement of the electromotive force which complys with Nernst formula, nitrates or nitrites are used as an electrode material and then the durable temperature of the sensor is limited by the melting point of nitrates or nitrites. Even when $Ba(NO_3)_2$, having the highest melting point is used as an electrode, the durable temperature is below 592° C. Furthermore, due to the diliquescence property of nitrates and nitrites, performance and stability of the sensor were not enough when used in the test gas containing water vapor.

For resolving above issues, a $NO_x$ sensor using an oxide of 6a Group element and oxides of perovskite or pseudo perovskite as an electrode material is proposed. These sensors have a good thermnal durability due to the high melting point and decomposition temperature of the oxides. However, the response of the $NO_x$ sensor of this type is different from that of the sensor using nitrate as an electrode which complys with Nernst formula and depends on the change of electromotive force caused by the catalytic activity of the electrode for the test gas and oxidation reduction reactions on the electrode and hence the performance of the sensor depends largely on the oxides. For example, electrodes using oxides of perovskite or pseudo perovskite structure containing Sn or Cu respond not only to $NO_x$ but also $CO_2$ and there are issues that the exact detection of $NO_x$ concentration is not possible, since it is affected very much by the $CO_2$ concentration. And a sensor using oxides of 6a Group element and perovskite structure containing Ti as an electrode works well around 500° C., but its sensitivity to $NO_x$ rapidly decreases above 600° C. and there are issues in the reduction of resolution and accuracy of $NO_x$ concentration.

DISCLOSURE OF THE PRESENT INVENTION

The present invention provides a $NO_x$ sensor which does not respond to $CO_2$ and has a good sensitivity to $NO_x$ at a temperature above 600° C.

The present invention proposes a $NO_x$ sensor using oxgen ion conductive solid electrolyte, whereon a pair of the first and the second electrodes are formed characterized in that at least the first electrode is composed of oxides of 7a or 8a Group element or a substance containing said oxides and that the first electrode is composed of hybrid oxides containing 7a or 8a Group element or of a substance containing said oxides.

In a more concrete form of the $NO_x$ sensor of the present invention, zirconia ($ZrO_2$—$M_2 O_3$ or $ZrO_2$—MO, Mi is Yb, Cd, Nd, Ca, Y, Mg, Hf) bismuth oxide ($Bi_2 O_3$—$M_2 O_3$ or MO or $M_2 O_5$, M is Y, Gd, Nb, W, Sr, Ba) and ceria oxide ($CeO_2$—$M_2 O_3$ or $MO_2$, M is Y, Sm) are used as a solid electrolyte. A solid electrolyte can be either a separation wall structure which separates the test gas to be detected of $NO_x$ concentration from the constant atmospheric gas such as air, a plate or rod shape. In case a solid electrolyte is a separation wall structure, the first and second electrode are placed on each surface of the wall and in the case that a solid electrolyte is not a separation wall structure, the first and second electrodes are placed at any place on the solid electrolyte.

The first electrode to be formed on an electrolyte is composed either of oxides of Mn, Fe, Co and Ni or a substance containing said oxide. Furthermore, the first electrode is composed either of hybridized oxides expressed by $ABO_3$, $AB_2 O_4$, $A_2 BO_4$ and $ACB_4$ or a substance containing said hybridized oxides. Here, B is an element selected from 7a or 8a Group and A and C are elements selected from 2A, 3A, 4A, 5A, 6A, 8, 1B, 2B, 3B, 4B, 5B Group and lanthanide. A part of A and C element of the hybrid oxides can be replaced by an element having similar ion radius or an element with same or close in valency and furthermore a part of B of said hybrid oxides can be replaced by an element having similar ion radius or an element with same or close in valency. The oxygen content expressed by the chemical formula can be a stoichiometric value including a non-integral number caused by the oxygen deficiency. These hybrid oxides can be a mixture of a single oxide of the element composing of hybrid oxides so far as hybrid oxides are the main component. If required, an electric collector composed of rare metals such as Pt, Au, Pd, Ir, Rh, Ru or its alloy as an electro-conductive material can be formed to keep electrical connection.

The first electrode of an oxide or a hybrid oxide is formed on a solid electrolyte by coating using screen printing, etc., and sintering and also it can be formed by physical deposition method such as vacuum deposition, lasor ablation, ion beam deposition and ionplating method and chemical deposition method such as chemical vapour phase deposition and plasma chemical vapour phase deposition.

The second electrode is composed of a substance comprising rare metals, such as Pt, Ag, Au, Pd, Ir, Rh and Ru, its alloy, electro-conductive ceramics, for example, oxides of perovskite structure expressed by $ABO_3$, such as $LaCoO_3$, $LaNiO_3$, $LaFeO_3$, wherein a part of A or B site can be replaced by an element such as Sr, an oxide having a structure of $K_2NiF_4$ and a substance which can be an oxygen electrode such as $La_2CuO_4$ or a substance which can give a definite chemical potential to oxygen. However, in a sensor wherein both the first and second electrode are exposed in the test gas, it is required that the change of the electrical potential caused at the first electrode should not be cancelled by the change of the electrical potential caused by the second electrode and it is preferred that it is composed of a material which does not cause a change of electrical potential for NO and $NO_2$ or a material which cause a change of electrical potential in an opposite direction to that caused at the first electrode.

In an electromotive force type sensor, wherein a pair of electrodes is formed on a solid electrolyte and the difference of the electrical potential caused by the difference in the chemical potential of the electrodes, the first electrode which works as a detecting electrode, reacts with the test gas existing on the surface of the electrode and as a result, the difference in the electrical potential is caused by the change of the chemical potential of the ion conductive carrier of a solid electrolyte to the chemical potential of the other electrode, which complys with the Nernst formula. However, the change of the electromotive force in the present invention does not comply with the Nernst formula, because the number of the electrons obtained from the slope of the dependency of the electromotive force on the concentration and temperature are not integral numbers. In a $NO_x$ sensor according to the present invention, the change of the electromotive force is different for $NO_2$ and NO. The electromotive force increases depending on the increase of the concentration of $NO_2$ and decreases depending on the increase of NO concentration. Judging from the change of the electromotive force corresponding to the change of the concentration of the test gas, it is thought that the reduction reaction of the test gas occurs on the electrode when the electromotive force increases and oxydation reaction occurs on the electrode when the electromotive force decreases. Furthermore, the dependency of the electromotive force on the concentration of $NO_x$ is different in the presence and absence of oxygen, wherein the slope of the dependency of the electromotive force on $NO_x$ concentration in the presence of oxygen is larger than that in the absence of oxygen; that is oxygen is involved in the electrode reaction. Namely the response of the sensor according to the present invention is obtained by the following reactions. On the first electrode, an electrochemical reaction between oxygen and $NO_x$ is concomitantly occurs and the change of the electromotive force is caused by the hybrid electropotential of the local battery formed on the first electrode. Namely, a hybrid electric potential is caused for $NO_2$ by the following reactions on the first electrode $$NO_2 + 2e \rightarrow NO + O^{2-} \quad (1)$$

$$O^{2-} \rightarrow \tfrac{1}{2}O_2 + 2e \quad (2)$$

and a hybrid electric potential is caused for NO by the following reactions on the first electrode $$\tfrac{1}{2}O_2 + 2e \rightarrow O^{2-} \quad (3)$$

$$NO + O^{2-} \rightarrow NO_2 + 2e \quad (4)$$

To obtain the electromotive force by the hybrid electric potential, it is necessary that the two reactions occur concomitantly on the electrode either for $NO_2$ and NO and the hybrid electric potential can not be obtained; if it is active for a reaction and not active for another reaction. Since the $NO_x$ sensor according to the present invention is composed of an oxide of 7a or 8 Group element, which is used as an oxygen electrode in a fuel battery or oxygen sensor and hybrid oxides containing 7a or 8 Group element, it is possible to act as an oxygen electrode and has an enough activity for the reactions of (2) and (4). Furthermore, oxides of 7a and 8 Group element and hybrid oxides containing 7a and 8 Group element also have a high catalytic activity for $NO_x$ and are active for the reactions of (1) and (2). Namely, since it is active both for oxygen and $NO_x$, the change of the electromotive force is obtained by the hybrid electric potential caused by the electrochemical reaction between oxygen and $NO_x$ which occurs concomitantly on the first electrode and occurs also at 600° C., and hence a good performance is obtained. On the other hand, it is thought that a hybrid electric potential is caused for $CO_2$ gas by the same reaction for $NO_2$. However, the catalytic activity of the electrode according to the present invention is low for $CO_2$ and electrochemical reaction between oxygen and $CO_2$ does not occur concomitantly on the first electrode and hence it does not respond to $CO_2$

PREFERRED EMBODIMENT OF THE PRESENT INVENTION

EXAMPLE 1

Figure 1:
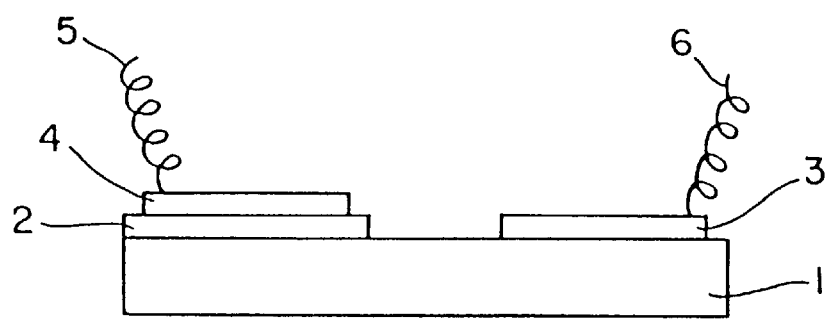
FIG. 1 is a cross section of an example of a $NO_x$ sensor according to the present invention.

FIG. 1 shows a cross section of a $NO_x$ sensor in an example according to the present invention. A solid electrolyte 1 can be any oxgen ion conductive material, however, in view of thermal stability and resistance, zirconia, wholly or partially stabilized by yttria, calcia or magnecia, etc. is preferred. In this example, zirconia stabilized by 8 mol % of yttria was used. On one surface of a plate solid electrolyte, the first electrode 2 and second electrode 3 are placed. The first electrode 2 is composed of oxides of 7a or 8a Group element. The first electrode was prepared by sputtering using oxide as a target. After preparation of a film by sputtering, heat treatment was conducted for 1 hr at 900° C. in the air. The second electrode 3 is composed of an electrode which does not respond to $NO_x$ and Pt is used in this case. The first electrode 2 and the second electrode 3 is a so called gas electrode and formed as a porous electrode. An electric collector 4 of Pt is placed on the first electrode 2 and the cable 5 and 6 of the second electrode 3 is connected with the measurement circuit.

Figure 2:
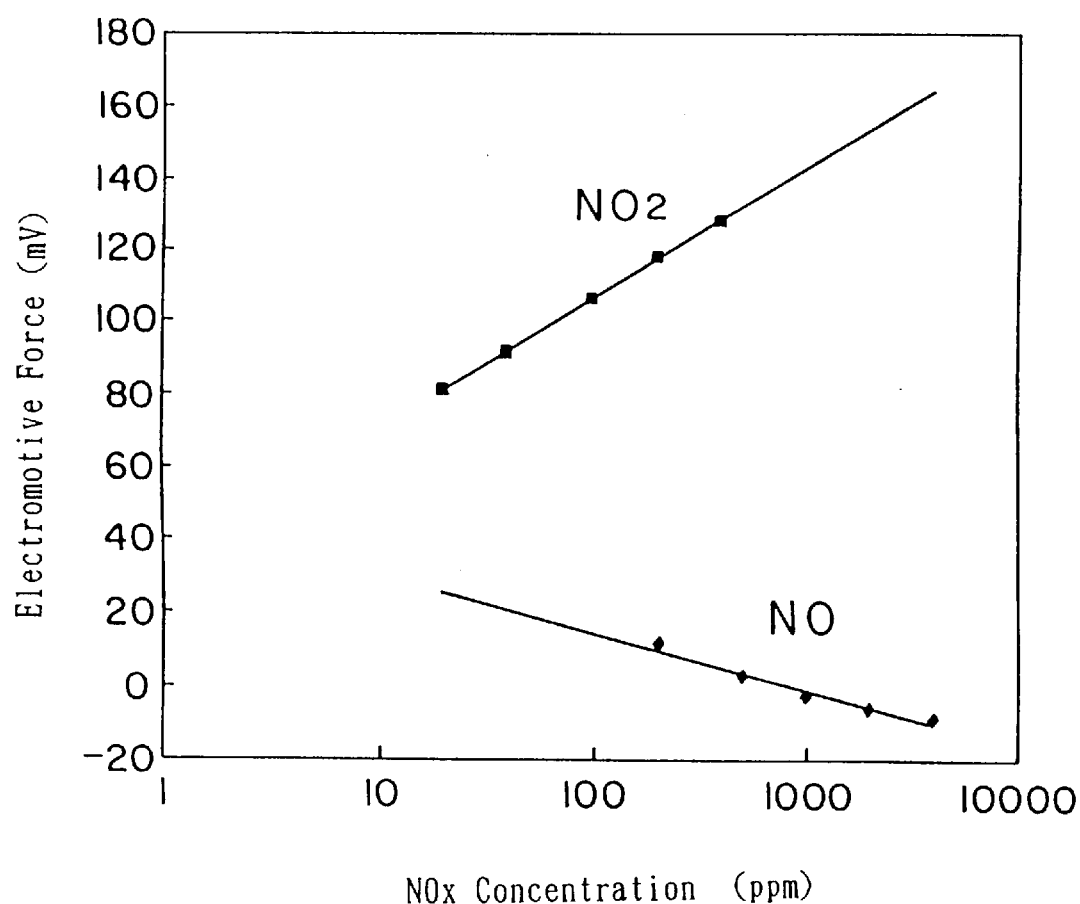
FIG. 2 is a figure showing the dependency of the change of the electromotive force on $NO_x$ concentration in an example of a $NO_x$ sensor according to the present invention.
Figure 3:
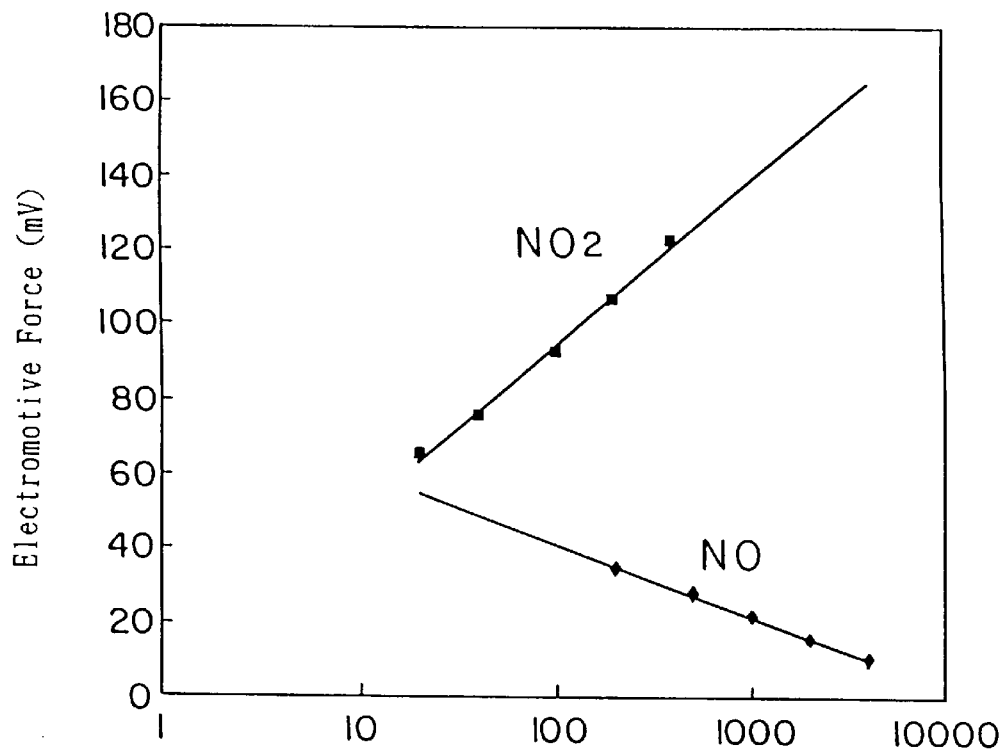
FIG. 3 is a figure showing the dependency of the change of the electromotive force on the $NO_x$ concentration in an example of a $NO_x$ sensor according to the present invention.
Figure 4:
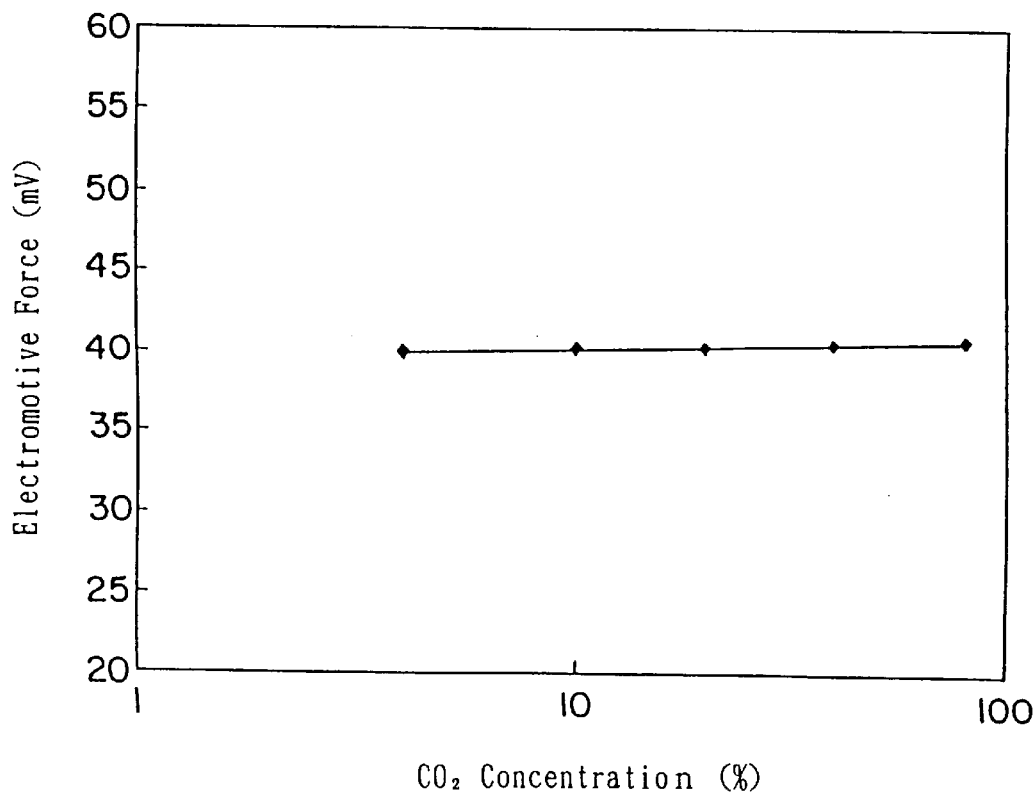
FIG. 4 is a figure showing the dependency of the change of the electromotive force on the $CO_2$ concentration.

The change of the electromotive force at the introduction of 100 ppm of $NO_2$ and 500 ppm of NO taking the value of the electromotive force under the atmospheric circumstance of 4% oxygen at 600° C. as a standard is shown in Table 1. The $NO_x$ sensor, whichever oxides are used, responds to $NO_2$ resulting in the increase of the electromotive force and to NO in the decrease of the electromotive force. Among oxides, the sensor using Co as the first electrode showed the heighest sensitivity. FIGS. 2 and 3 show the dependency of the electromotive force of a $NO_x$ sensor using oxides of Co as the first electrode on $NO_x$ concentration. FIG. 4 shows the dependency of the electromotive force of a $NO_x$ sensor using oxides of Co as the first electrode on $CO_2$ concentration at 600° C. The sensor does not respond to $CO_2$ and the electromotive force does not change even when $CO_2$ concentration changes. The dependency of the electromotive force on $NO_x$ concentration and the responce characteristic to $CO_2$ were same for the sensor using other oxides shown in this example.

TABLE 1

The Change of the Electromotive Force corresponding to 100 ppm $NO_2$ and 500 ppm No

| Electrode Material | The Change of the Electromotive Force (mV) | |
| --- | --- | --- |
| | 100 ppm $NO_2$ | 500 ppm NO |
| $Mn_2O_3$ | 16.9 | −10.5 |
| $Fe_2O_3$ | 28.7 | −11.5 |
| $Co_3O_4$ | 64.3 | −38.1 |
| NiO | 43.8 | −10.1 |

EXAMPLE 2

Figure 5:
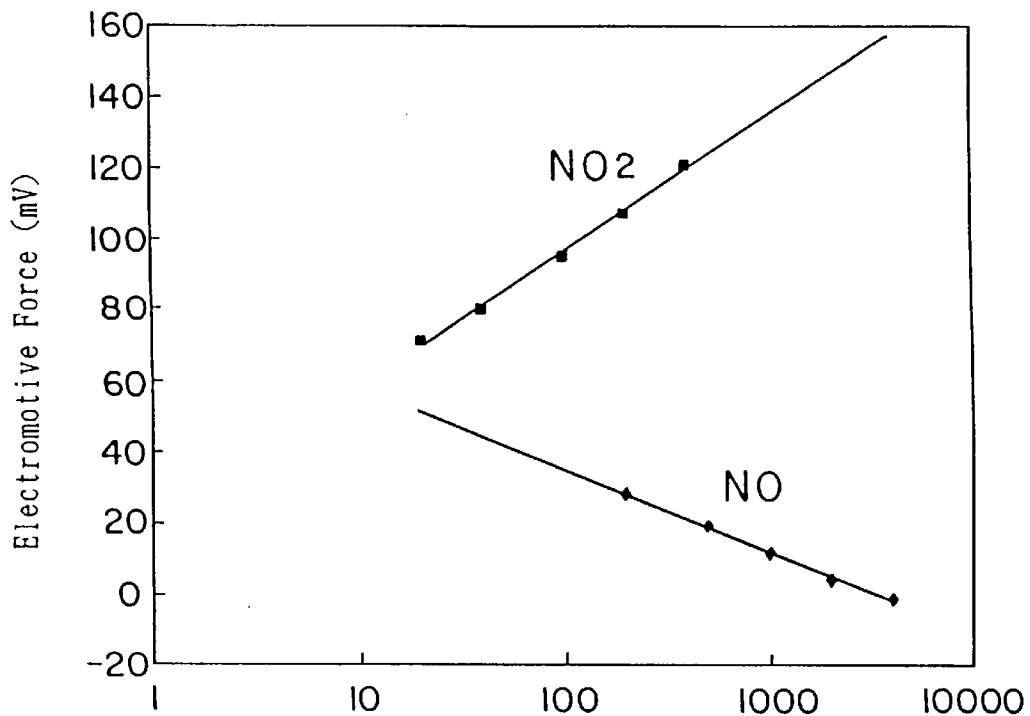
FIG. 5 is a figure showing the dependency of the change of the electromotive force on the $NO_x$ sensor according to the present invention.

A $NO_x$ sensor was prepared using hybrid oxides expressed by the same method as explained in Example 1. Hybrid oxides expressed by $ABO_3$ used as the first electrode were prepared by sintering a mixture of a single oxide of each element composing of hybrid oxides. It was confirmed by the X-ray diffraction that these hybrid oxides are composed of a single phase or a mixed phase of oxides of either A or B. The change of electromotive force at the introducing of 100 ppm of $NO_2$ and 500 ppm of NO taking the value of the electromotive force under the atmospheric circumstance of 4% oxygen at 600° C. as a standard is shown in Table 2. A $NO_x$ sensor using hybrid oxides expressed by $ABO_3$ as the first electrode responds to $NO_2$ resulting in the increase of the electromotive force and to NO in the decrease of the electromotive force and the change of the electromotive force to the concentration of $NO_2$ and NO was proportional to the logarism of the concentration. Furthermore, any of the sensors did not respond to $CO_2$. FIG. 5 shows the dependency of the electromotive force of a $NO_x$ sensor at 600° C. on $NO_x$ concentration.

TABLE 2

The Change of the Electromotive Force corresponding to 100 ppm $NO_2$ and 500 ppm NO

| Electrode Material | The Change of the Electromotive Force (mV) | |
| --- | --- | --- |
| | 100 ppm $NO_2$ | 500 ppm NO |
| $MgMnO_3$ | 37.4 | −18.2 |
| $SrMnO_3$ | 66.1 | −11.4 |
| $CaMnO_3$ | 30.5 | −14.5 |
| $BaMnO_3$ | 43.6 | −12.8 |
| $YMnO_3$ | 25.3 | −11.8 |
| $CrMnO_3$ | 32.2 | −10.0 |
| $CoMnO_3$ | 36.8 | −17.4 |
| $NiMnO_3$ | 52.4 | −25.7 |
| $AgMnO_3$ | 32.1 | −13.5 |
| $ZnMnO_3$ | 57.5 | −35.6 |
| $LaMnO_3$ | 44.8 | −25.7 |
| $NdMnO_3$ | 35.4 | −18.7 |
| $SmMnO_3$ | 39.0 | −10.7 |
| $(YSr)MnO_3$ | 22.6 | −10.5 |
| $GaFeO_3$ | 21.8 | −9.2 |
| $LaFeO_3$ | 49.3 | −19.8 |
| $LaCoO_3$ | 45.2 | −20.1 |
| $LaNiO_3$ | 22.4 | −11.2 |
| $SrNiO_3$ | 28.6 | −10.9 |

EXAMPLE 3

Figure 6:
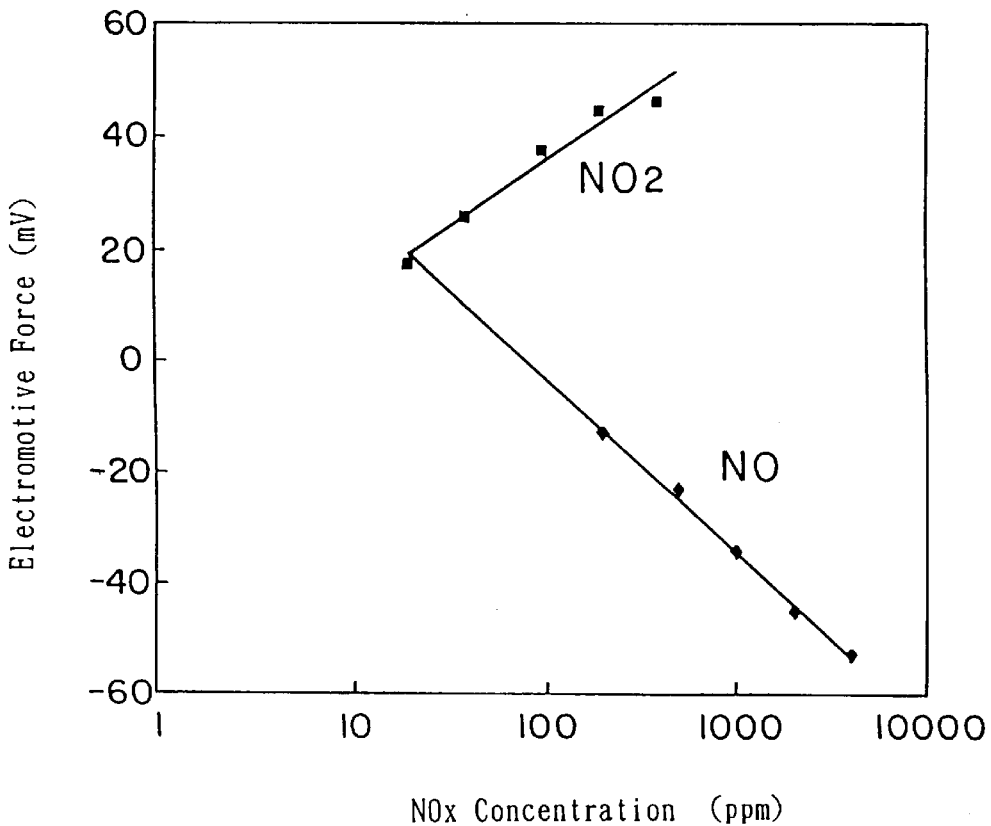
FIG. 6 is a figure showing the dependency of the change of the electromotive force on $NO_x$ concentration in an example of a $NO_x$ sensor according to the present invention.

A Nox sensor was preapred using hybrid oxides exp essed by $AB_2O_4$ as the first electrode by the same method as shown in Example 2. The change of the electromotive force at the introduction of 100 ppm of $NO_2$ and 500 ppm of NO taking the value of the electromotive force under the atmospheric circumstance of 4% oxygen at 600° C. as a standard is shown in Table 3. In this example, it was also confirmed that the sensor responds $NO_2$ resulting in the increase of the electromotive force and to NO in the decrease of the electromotive force and the change of the electromotive force to the concentration of $NO_2$ and NO was proportional to the logarism of the concentration. Any sensor did not responds to $CO_2$ at the first electrode. In FIG. 6, the dependency of the electromotive force of a $NO_x$ sensor using $CdMn_2O_4$ as the first electrode on $NO_x$ concentration at 600° C. is shown.

TABLE 3

The Change of the Electromotive Force corresponding to 100 ppm $NO_2$ and 500 ppm NO

| Electrode Material | The Change of the Electromotive Force (mV) | |
| --- | --- | --- |
| | 100 ppm $NO_2$ | 500 ppm NO |
| $MgMn_2O_4$ | 35.5 | −16.1 |
| $TiMn_2O_4$ | 25.4 | −11.8 |
| $CrMn_2O_4$ | 28.2 | −17.1 |
| $CoMn_2O_4$ | 29.7 | −15.9 |
| $CdMn_2O_4$ | 47.9 | −30.6 |
| $(CdAl)Mn_2O_4$ | 46.8 | −25.6 |
| $(CdAl)(MnCr)_2O_4$ | 10.8 | −19.4 |
| $CdFe_2O_4$ | 18.0 | −10.2 |
| $ZnFe_2O_4$ | 34.5 | −18.6 |
| $CrFe_2O_4$ | 26.7 | −12.3 |

EXAMPLE 4

Figure 7:
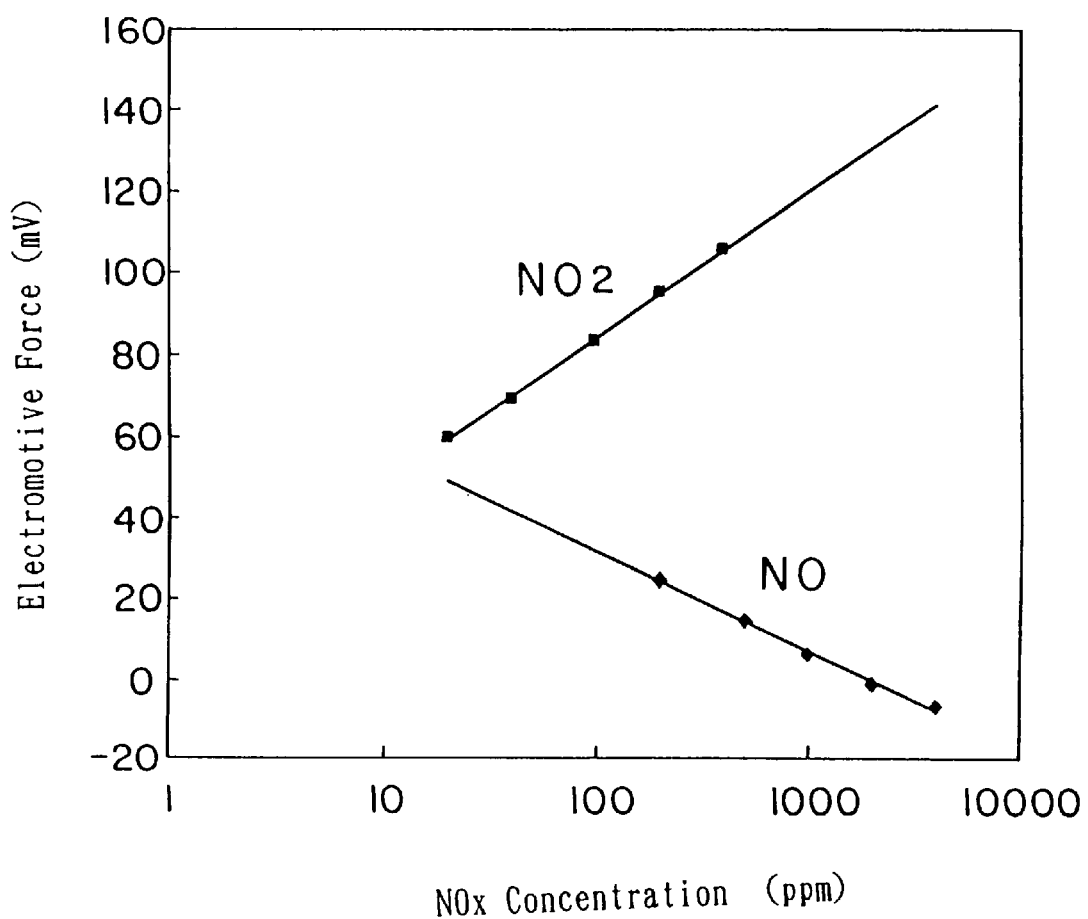
FIG. 7 is a figure showing the dependency of the change of the electromotive force on $NO_x$ concentration in an example of a $NO_x$ sensor according to the present invention.

A $NO_x$ sensor was prepared using hybrid oxides expressed by $A_2BO_4$ as the first electrode by the same method as explained in Example 2 and the change of the electromotive force at the introduction of 100 ppm of $NO_2$ and 500 ppm of NO taking the value of the electromotive force under the atmospheric circumstance of 4% oxygen at 600° C. as a standard is shown in Table 4. In this example, it was also confirmed that the sensor responds the $NO_2$ resulting in the increase of the electromotive force and to NO in the decrease of the electromotive force and the change of the electromotive force to the concentration of $NO_2$ and NO was proportional to the logarithm of the concentration. In FIG. 7, the dependency of the change of electromotive force at 600° C. of a $NO_x$ sensor using $La_2MnO_2$ as the first electrode is shown.

TABLE 4

The Change of the Electromotive Force corresponding to 100 ppm $NO_2$ and 500 ppm NO

| Electrode Material | The Change of the Electromotive Force (mV) | |
|---|---|---|
| | 100 ppm $NO_2$ | 500 ppm NO |
| $Ca_2MNO_4$ | 33.1 | −14.1 |
| $Mg_2MnO_4$ | 29.5 | −12.2 |
| $Fe_2MnO_4$ | 33.8 | −14.0 |
| $Ni_2MnO_4$ | 56.7 | −10.2 |
| $Zn_2MnO_4$ | 50.0 | −17.6 |
| $Al_2MnO_4$ | 28.6 | −11.9 |
| $Sb_2MnO_4$ | 58.2 | −10.4 |
| $La_2MnO_4$ | 44.8 | −25.7 |
| $Cr_2CoO_4$ | 55.1 | −18.8 |

EXAMPLE 5

A $NO_x$ sensor was prepared using hybrid oxides expressed by $ABCO_4$ as the first electrode by the same method as explained in Example 1 and the change of the electromotive force at the introduction of 100 ppm of $NO_2$ and 500 ppm of NO taking the value of the electromotive force under the atmospheric circumstance of 4% oxygen at 600° C. as a standard is shown in Table 5.

In this example it was also confirmed that the sensor responds to $NO_2$ resulting in the increase of the electromotive force and to NO in the decrease of the electromotive force and the change of the electromotive force to the concentration of $NO_2$ and NO was proportional to the logarism of the concentration. Either of the electrodes did not respond to $CO_2$.

TABLE 5

The Change of the Electromotive Force corresponding to 100 ppm $NO_2$ and 500 ppm NO

| Electrode Material | The Change of the Electromotive Force (mV) | |
|---|---|---|
| | 100 ppm $NO_2$ | 500 ppm NO |
| $CdGaMnO_4$ | 44.7 | −26.3 |
| $YFeMnO_4$ | 40.3 | −16.6 |

Possible Utilization of the Invention in the Industry

Since oxides or hybrid oxides which have no catalytic activity for $CO_2$ are used as the electrode material, it is possible to detect $NO_x$ concentration correctly without being affected by the fluctuation of $CO_2$ concentration. Furthermore, those oxides or hybrid oxides are active both for oxygen and $NO_x$ and hence the sensor looks at a temperature above 600° C. and detects $NO_x$ concentration with high accuracy.

We claim:

1. An $NO_x$ sensor consisting essentially of first and second electrodes in contact with a solid electrolyte, wherein said sensor is capable of detecting a concentration of $NO_x$ in a gas by converting an amount of $NO_x$ concentration into an electromotive force level between the first and second electrodes, wherein the electromotive force linearly increases in response to an increase, in terms of a logarithm, of $NO_2$ concentration and linearly decreases in response to an increase, in terms of a logarithm, of NO concentration, wherein at least said first electrode is selected from the group consisting of $Mn_2O_3$, $CdFe_2O_4$, $ZnFe_2O_4$, $CrFe_2O_4$, $Cr_2CoO_4$, $CdGaMnO_4$ and $YFeMnO_4$.

2. The $NO_x$ sensor of claim 1, wherein said second electrode is (1) a metal selected from the group consisting of Pt, Ag, Au, Pd, Ir, Rh and Ru, (2) an alloy of metal (1), or (3) an electro-conductive ceramic.

* * * * *